(12) United States Patent
Laas et al.

(10) Patent No.: US 10,752,723 B2
(45) Date of Patent: *Aug. 25, 2020

(54) POLYISOCYANURATE POLYMER AND PROCESS FOR THE PRODUCTION OF POLYISOCYANURATE POLYMERS

(71) Applicant: Covestro Deutschland AG, Leverkusen (DE)

(72) Inventors: Hans-Josef Laas, Odenthal (DE); Dieter Mager, Leverkusen (DE); Mathias Matner, Neuss (DE); Dirk Achten, Leverkusen (DE); Heiko Hocke, Shanghai (CN)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/568,110

(22) PCT Filed: Apr. 21, 2016

(86) PCT No.: PCT/EP2016/058904
§ 371 (c)(1),
(2) Date: Oct. 20, 2017

(87) PCT Pub. No.: WO2016/170059
PCT Pub. Date: Oct. 27, 2016

(65) Prior Publication Data
US 2018/0134835 A1     May 17, 2018

(30) Foreign Application Priority Data

Apr. 21, 2015   (EP) .................................. 15164520

(51) Int. Cl.
| | | |
|---|---|---|
| *C08G 18/79* | (2006.01) | |
| *C08G 18/02* | (2006.01) | |
| *C07D 251/34* | (2006.01) | |

(52) U.S. Cl.
CPC ......... *C08G 18/022* (2013.01); *C08G 18/027* (2013.01); *C08G 18/792* (2013.01); *C07D 251/34* (2013.01)

(58) Field of Classification Search
CPC ... C08G 18/792; C08G 18/022; C08G 18/027
See application file for complete search history.

(56) References Cited

U.S. PATENT DOCUMENTS

| | | |
|---|---|---|
| 3,211,703 A | 10/1965 | Gilman et al. |
| 3,330,828 A | 7/1967 | Grogler et al. |
| 3,487,080 A | 12/1969 | Matsui et al. |
| 3,640,937 A | 2/1972 | Thoma et al. |
| 3,640,967 A | 2/1972 | König et al. |
| 3,658,746 A | 4/1972 | Rosendahl et al. |
| 3,996,223 A | 12/1976 | Gupta et al. |
| 4,040,992 A | 8/1977 | Bechara et al. |
| 4,255,569 A | 3/1981 | Muller et al. |
| 4,288,586 A | 9/1981 | Bock et al. |
| 4,324,879 A | 4/1982 | Bock et al. |
| 4,379,905 A | 4/1983 | Stemmler et al. |
| 4,419,513 A | 12/1983 | Breidenbach et al. |
| 4,487,928 A | 12/1984 | Richter et al. |
| 4,499,253 A | 2/1985 | Kerimis et al. |
| 4,604,418 A | 8/1986 | Shindo et al. |
| 4,613,686 A | 9/1986 | König et al. |
| 4,789,705 A | 12/1988 | Kase et al. |
| 4,808,691 A | 2/1989 | König et al. |
| 4,837,359 A | 6/1989 | Woynar et al. |
| 4,960,848 A | 10/1990 | Scholl et al. |
| 4,994,541 A | 2/1991 | Dell et al. |
| 5,013,838 A | 5/1991 | Scholl |

(Continued)

FOREIGN PATENT DOCUMENTS

| | | |
|---|---|---|
| CA | 2034622 A1 | 8/1991 |
| CA | 2139535 A1 | 8/1995 |

(Continued)

OTHER PUBLICATIONS

International Preliminary Report on Patentability for PCT/EP2016/058901 dated Oct. 24, 2017.
International Preliminary Report on Patentability for PCT/EP2016/058902 dated Oct. 24, 2017.
International Preliminary Report on Patentability for PCT/EP2016/058904 dated Oct. 24, 2017.
International Preliminary Report on Patentability for PCT/EP2016/058905 dated Oct. 24, 2017.
International Preliminary Report on Patentability for PCT/EP2016/058906 dated Oct. 24, 2017.
International Search Report for PCT/EP2016/058901 dated Jun. 30, 2016.

(Continued)

*Primary Examiner* — Michael L Leonard
(74) *Attorney, Agent, or Firm* — Faegre Drinker Biddle & Reath LLP

(57) ABSTRACT

The present invention relates to novel polyisocyanurate plastics which are obtainable by catalytic trimerization of a polyisocyanate composition A) which contains oligomeric polyisocyanates and is low in monomeric diisocyanates. "Low in monomeric diisocyanates" means that the polyisocyanate composition A) has a content of monomeric diisocyanates of at most 20% by weight. The invention further relates to the use of these polyisocyanurate plastics for production of coatings, films, semi-finished products and mouldings, and to a process for producing polyisocyanurate plastics comprising the following steps: (a) providing a polyisocyanate composition A) which contains oligomeric polyisocyanates and is low in monomeric diisocyanates, "low in monomeric diisocyanates" meaning that the polyisocyanate composition A) has a content of monomeric diisocyanates of at most 20% by weight; (b) catalytically trimerizing the polyisocyanate composition A).

4 Claims, No Drawings

(56) References Cited

U.S. PATENT DOCUMENTS

| | | | |
|---|---|---|---|
| 5,064,960 A | 11/1991 | Pedain et al. | |
| 5,076,958 A | 12/1991 | Pedain et al. | |
| 5,115,071 A * | 5/1992 | Quay | C08G 18/10 528/59 |
| 5,489,663 A | 2/1996 | Brandt et al. | |
| 5,914,383 A | 6/1999 | Richter et al. | |
| 6,090,939 A | 7/2000 | Richter et al. | |
| 6,133,397 A | 10/2000 | O'Connor et al. | |
| 6,251,985 B1 | 6/2001 | Wamprecht et al. | |
| 6,613,863 B2 | 9/2003 | Kohlstruk et al. | |
| 6,635,761 B1 | 10/2003 | Revelant et al. | |
| 6,765,111 B1 * | 7/2004 | Pedain | C07D 251/34 544/193 |
| 8,119,799 B2 | 2/2012 | Binder et al. | |
| 2003/0130467 A1 * | 7/2003 | Dallemer | C08G 18/022 528/44 |
| 2009/0234091 A1 * | 9/2009 | Richter | B01J 31/0267 528/51 |
| 2010/0056702 A1 | 3/2010 | Grahl et al. | |
| 2011/0201707 A1 * | 8/2011 | Athey | C08G 18/022 521/108 |
| 2013/0303758 A1 | 11/2013 | Lucas et al. | |
| 2015/0158966 A1 | 6/2015 | Laas et al. | |
| 2017/0044296 A1 | 2/2017 | Harada | |
| 2017/0121225 A1 * | 5/2017 | Zielinski | C04B 24/282 |

FOREIGN PATENT DOCUMENTS

| | | |
|---|---|---|
| CA | 2244486 A1 | 2/1999 |
| CA | 2253119 A1 | 5/1999 |
| DE | 1570540 A1 | 3/1970 |
| DE | 1954093 A1 | 6/1970 |
| DE | 1902931 A1 | 8/1970 |
| DE | 1918204 A1 | 9/1970 |
| DE | 1670666 A1 | 7/1971 |
| DE | 1770245 A1 | 10/1971 |
| DE | 1770591 A1 | 11/1971 |
| DE | 1667309 A1 | 9/1972 |
| DE | 2414413 A1 | 10/1975 |
| DE | 2446440 A1 | 4/1976 |
| DE | 2452532 A1 | 5/1976 |
| DE | 2631733 A1 | 2/1977 |
| DE | 2641380 A1 | 3/1978 |
| DE | 3100263 A1 | 8/1982 |
| DE | 3219608 A1 | 9/1983 |
| DE | 3240613 A1 | 5/1984 |
| DE | 8711301 U1 | 10/1987 |
| DE | 3700209 A1 | 7/1988 |
| DE | 3717060 A1 | 12/1988 |
| DE | 3900053 A1 | 7/1990 |
| DE | 3928503 A1 | 3/1991 |
| DE | 10142816 A1 | 7/2002 |
| EP | 0003765 A1 | 9/1979 |
| EP | 0010589 A1 | 5/1980 |
| EP | 0013880 A1 | 8/1980 |
| EP | 0033581 A1 | 8/1981 |
| EP | 0047452 A1 | 3/1982 |
| EP | 0056158 A1 | 7/1982 |
| EP | 0056159 A1 | 7/1982 |
| EP | 0100129 A1 | 2/1984 |
| EP | 0102482 A2 | 3/1984 |
| EP | 0150769 A2 | 8/1985 |
| EP | 0330966 A2 | 9/1989 |
| EP | 0336205 A2 | 10/1989 |
| EP | 0339396 A1 | 11/1989 |
| EP | 0377177 A1 | 7/1990 |
| EP | 0379914 A2 | 8/1990 |
| EP | 0443167 A1 | 8/1991 |
| EP | 0496208 A2 | 7/1992 |
| EP | 0668271 A1 | 8/1995 |
| EP | 0671426 A1 | 9/1995 |
| EP | 0798299 A1 | 10/1997 |
| EP | 0896009 A1 | 2/1999 |
| EP | 0899282 A2 | 3/1999 |
| EP | 0916647 A2 | 5/1999 |
| EP | 0962455 A1 | 12/1999 |
| EP | 1229016 A2 | 8/2002 |
| EP | 1599526 A1 | 11/2005 |
| EP | 2159238 A1 | 3/2010 |
| EP | 2883895 A1 | 6/2015 |
| GB | 809809 A | 3/1959 |
| GB | 952931 A | 3/1964 |
| GB | 966338 A | 8/1964 |
| GB | 1145952 A | 3/1969 |
| GB | 1244416 A | 9/1971 |
| GB | 1335958 A | 10/1973 |
| GB | 1386399 A | 3/1975 |
| GB | 1391066 A | 4/1975 |
| GB | 1462597 A | 1/1977 |
| GB | 2221465 A | 2/1990 |
| GB | 2222161 A | 2/1990 |
| JP | 2001098042 A | 4/2001 |
| WO | WO-1999023128 A1 | 5/1999 |
| WO | WO-2004078820 A1 | 9/2004 |
| WO | WO-2005087828 A1 | 9/2005 |
| WO | WO-2013167404 A1 | 11/2013 |
| WO | WO-2015166983 A1 | 11/2015 |

OTHER PUBLICATIONS

International Search Report for PCT/EP2016/058902 dated Jul. 14, 2016.

International Search Report for PCT/EP2016/058904 dated Jul. 13, 2016.

International Search Report for PCT/EP2016/058905 dated Jul. 8, 2016.

International Search Report for PCT/EP2016/058906 dated Jul. 13, 2016.

Written Opinion of the International Searching Authority for PCT/EP2016/058901 dated Jun. 30, 2016.

Written Opinion of the International Searching Authority for PCT/EP2016/058902 dated Jul. 14, 2016.

Written Opinion of the International Searching Authority for PCT/EP2016/058904 dated Jul. 13, 2016.

Written Opinion of the International Searching Authority for PCT/EP2016/058905 dated Jul. 8, 2016.

Written Opinion of the International Searching Authority for PCT/EP2016/058906 dated Jul. 13, 2016.

Cinnamon, S., et al., "Adhesion Properties of Poly(Hexamethylene Diisocyanate) Obtained by Organotin Catalysis", European Polymer Journal, 1908, vol. 16, pp. 147-148.

Dabi, S., et al., "Foam Polymerization of Hexamethylene Diisocyanate by Cobalt Naphthenate", European Polymer Journal, 1982, vol. 18, pp. 549-553.

Dabi, S., et al., "Oligomerization of Hexamethylene Diisocyanate by Organometiallic Catalysts", European Polymer Journal, 1980, vol. 16, pp. 831-833.

Flipsen, T., "Design, Synthesis and Properties of New Materials Based on Densely Crosslinked Polymers for Polymer Optical Fiber and Amplifier Applications", Rijksuniversiteit Groningen, University of Groningen, 2000, pp. 1-231.

Hakman, N., "Properties of Polyisocyanurate Resins Obtained by Polymerization of Hexamethylene Diisocyanate by Organotin Catalysts", European Polymer Journal, 1978, vol. 14, pp. 675-678.

Moritsugu, M., et al., "Cyclotrimerization of Diisocyanates Toward High-Performance Networked Polymers with Rigid Isocyanurate Structure: Combination of Aromatic and Aliphatic Diisocyanates for Tunable Flexibility", Journal of Polymer Science, 2013, vol. 51, pp. 2631-2637.

Schildknecht, C.E., et al., "Polymerization Processes", Wiley, New York, 1977, pp. 665-667.

Flipsen, T., "Design, Synthesis and Properties of New Materials Based on Densely Crosslinked Polymers for Polymer Optical Fiber and Amplifier Applications", University of Groningen Thesis, 2000, pp. 1-229.

* cited by examiner

POLYISOCYANURATE POLYMER AND PROCESS FOR THE PRODUCTION OF POLYISOCYANURATE POLYMERS

CROSS-REFERENCE TO RELATED APPLICATIONS

This application is a national stage application (under 35 U.S.C. § 371) of PCT/EP2016/058904, filed Apr. 21, 2016, which claims benefit of European Application No. 15164520.7, filed Apr. 21, 2015, both of which are incorporated herein by reference in their entirety.

The invention relates to polyisocyanurate plastics, to a process for production thereof and to the use thereof for production of coatings, films, semi-finished products or mouldings.

BACKGROUND OF THE INVENTION

Polymers having polyisocyanurate structure are known for their high thermal stability and flame resistance. Polyisocyanurate foams based on aromatic diphenylmethane 4,4'-diisocyanate (MDI) are in widespread use, particularly as high-performance insulating materials, for example because of their very low thermal conductivity. However, MDI polyisocyanurates, as is commonly known from aromatic polyurethanes, have only low light stability and have a tendency to significant yellowing.

There has therefore been no lack of attempts to synthesize polyisocyanurate plastics based on aliphatic light-resistant isocyanates.

For example, *European Polymer Journal, Vol.* 16, 147-148 (1980) describes the catalytic trimerization of monomeric 1,6-diisocyanatohexane (HDI) at 40° C. to give a clear transparent polyisocyanurate plastic free of isocyanate groups. For this purpose, however, 15% by weight of dibutyltin dimethoxide as trimerization catalyst is required. *European Polymer Journal,* Vol. 16, 831-833 (1980) describes the complete trimerization of monomeric HDI to give a polyisocyanurate at a temperature of 140° C. using 6% by weight of tributyltin oxide as catalyst.

*Journal of Polymer Science Part A: Polymer Chemistry* 2013, 51, 2631-2637 describes the production of optically transparent polyisocyanurate films based on monomeric HDI/MDI mixtures with sodium p-toluenesulphinate as catalyst. Using exclusively monomeric HDI as starting diisocyanate, however, it is not possible to obtain clear films with this catalyst, since the reaction mixture foams significantly because of the extreme exothermicity of the trimerization reaction. According to this publication, the synthesis of a pure HDI polyisocyanurate was possible only in a test tube on the mmol scale in organic solution after complex workup.

U.S. Pat. No. 3,211,703 describes solid crosslinked polymers consisting of at least ten successive isocyanurate structures joined via divalent aliphatic groups, preferably hexamethylene chains. In the specific working examples of this patent specification, however, exclusively copolymers of HDI with styrene oxide are described.

JP 2001-098042 describes polyisocyanurates proceeding from monomeric cycloaliphatic bis(isocyanatomethyl)norbornane (NBDI) which have an isocyanate group content of max. 13% in the end product and are prepared using a catalyst system consisting of potassium fluoride and a complexing agent containing ethylene oxide groups.

The thesis by Theo Flipsen: *"Design, synthesis and properties of new materials based on densely crosslinked polymers for polymer optical fiber and amplifier applications", Rijksuniversiteit Groningen,* 2000 describes the trimerization of monomeric HDI with a neodymium/crown ether complex as catalyst. The polyisocyanurate obtained, which is said to have good optical, thermal and mechanical properties, was studied in the context of the thesis for its suitability for optical applications, especially as polymeric optical fibres.

However, processes known from the prior art for production of polyisocyanurate plastics from monomeric aliphatic diisocyanates have the fundamental disadvantage that a considerable shrinkage in volume occurs in the course of a trimerization reaction, which can present problems particularly in the case of casting of bodies of defined geometry. Moreover, it is a common factor in the production processes for polyisocyanurate plastics which proceed from the monomeric diisocyanates and are known from the prior art that they are very time-consuming and take place in closed systems under complex temperature control.

WO 2015/166983 discloses the use of isocyanurate polymers for encapsulating LEDs. It is explicitly disclosed that only those isocyanurate polymers which contain allophanate groups have the required technical properties.

U.S. Pat. No. 6,133,397 only discloses coatings made by trimerizing oligomeric polyisocyanates. It does not disclose the production of solid bodies.

The problem addressed by the present invention was therefore that of providing novel polyisocyanurate plastics having high thermal stability, which can be produced with considerably lower volume contraction and are thus also suitable particularly for production of bodies with defined geometry.

BRIEF SUMMARY OF THE INVENTION

This object is achieved in accordance with the invention by the polyisocyanurate plastic specified in claim 1, the uses and products specified in claims 12 and 13 and the process specified in claim 14.

Advantageous configurations of the invention are specified in the dependent claims and are specifically elucidated in detail below, as is the general concept of the invention.

The invention relates to a polyisocyanurate plastic which is obtainable by catalytic trimerization of a polyisocyanate composition A) which contains (1.) oligomeric polyisocyanates and (2.) is low in monomeric diisocyanates, "low in monomeric diisocyanates" meaning that the polyisocyanate composition A) has a content of monomeric diisocyanates of at most 20% by weight.

The invention also further provides the process from which the polyisocyanurate plastics of the invention are obtainable. This comprises the following steps:
a) providing a polyisocyanate composition A) which contains oligomeric polyisocyanates and is low in monomeric diisocyanates, "low in monomeric diisocyanates" meaning that the polyisocyanate composition A) has a content of monomeric diisocyanates of at most 20% by weight;
b) catalytically trimerizing the polyisocyanate composition A).

In addition, the invention also provides for the use of the polyisocyanurate plastics of the invention for production of coatings, films, semi-finished products or mouldings.

DETAILED DESCRIPTION OF THE INVENTION

The invention described in detail hereinafter is based on the surprising observation that catalytic trimerization of low-monomer oligomeric polyisocyanate compositions affords novel polyisocyanurate plastics having many advantageous properties and have only comparatively low volume shrinkage, particularly during the curing process.

The use of low-monomer oligomeric polyisocyanate compositions rather than monomeric diisocyanates as starting materials for production of polyisocyanurate plastics additionally has the advantage that, because of the comparatively low isocyanate contents of the oligomeric reactants, much less heat of reaction has to be removed during the curing, which especially also facilitates the production of large-volume components. Moreover, the use of low-monomer polyisocyanate compositions containing oligomeric polyisocyanates as oligomeric reactants for the trimerization reaction also leads to a novel crosslinking structure in the polyisocyanurate plastic obtainable, which distinguishes it structurally from the materials known from the prior art.

A "polyisocyanurate plastic" as used here is a polymer containing polyisocyanurate. It may also consist predominantly or entirely of a polyisocyanurate. Blends of polyisocyanurates and other plastics are likewise covered by the term "polyisocyanurate plastic" as used here.

When reference is made here to "plastic", this means a product which is very substantially dimensionally stable at room temperature—in contrast, for example, to gels or liquids. The term "plastic" as used here encompasses all standard classes of plastic, i.e. especially including thermosets, thermoplastics and elastomers.

A "polyisocyanurate" as used here is any molecule, preferably a polymer, having a plurality of isocyanurate structural units, for example at least 10 isocyanurate structural units. A molecule having a single isocyanurate structural unit can be referred to as "isocyanurate".

The characteristic cyclic isocyanurate structural unit is shown in the following structural formula:

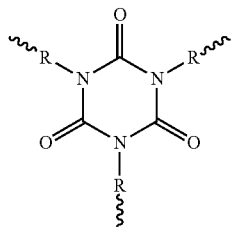

Isocyanurates and polyisocyanurates can be obtained by cyclotrimerization of polyisocyanates. The conventionally operated cyclotrimerization proceeding from monomeric diisocyanates is—as described above—a strongly exothermic reaction. This can considerably restrict the use options and the levels of trimerization that are still achievable industrially and efficiently.

The term "polyisocyanate" as used here is a collective term for compounds containing two or more isocyanate groups in the molecule (this is understood by the person skilled in the art to mean free isocyanate groups of the general structure —N=C=O). The simplest and most important representatives of these polyisocyanates are the diisocyanates. These have the general structure O=C=N—R—N=C=O where R typically represents aliphatic, alicyclic and/or aromatic radicals.

Because of the polyfunctionality (≥2 isocyanate groups), it is possible to use polyisocyanates to prepare a multitude of polymers (e.g. (e.g. polyurethanes, polyureas and polyisocyanurates) and low molecular weight compounds (for example those having uretdione, isocyanurate, allophanate, biuret, iminooxadiazinedione and/or oxadiazinetrione structure).

When general reference is made here to "polyisocyanates", this means monomeric and/or oligomeric polyisocyanates alike. For understanding of many aspects of the invention, however, it is important to distinguish between monomeric diisocyanates and oligomeric polyisocyanates. When reference is made here to "oligomeric polyisocyanates", this means polyisocyanates formed from at least two monomeric diisocyanate molecules, i.e. compounds that constitute or contain a reaction product formed from at least two monomeric diisocyanate molecules.

The preparation of oligomeric polyisocyanates from monomeric diisocyanates is also referred to here as modification of monomeric diisocyanates. This "modification" as used here means the reaction of monomeric diisocyanates to give oligomeric polyisocyanates having uretdione, isocyanurate, allophanate, biuret, iminooxadiazinedione and/or oxadiazinetrione structure.

For example, hexamethylene diisocyanate (HDI) is a "monomeric diisocyanate" since it contains two isocyanate groups and is not a reaction product of at least two polyisocyanate molecules:

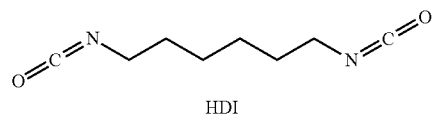

HDI

Reaction products which are formed from at least two HDI molecules and still have at least two isocyanate groups, by contrast, are "oligomeric polyisocyanates" within the context of the invention. Representatives of such "oligomeric polyisocyanates" are, proceeding from monomeric HDI, for example, HDI isocyanurate and HDI biuret, each of which are formed from three monomeric HDI units:

(idealized structural formulae)

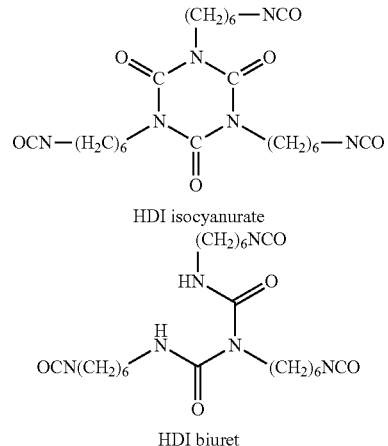

"Polyisocyanate composition A)" in the context of the invention refers to the isocyanate component in the initial reaction mixture. In other words, this is the sum total of all the compounds in the initial reaction mixture that have isocyanate groups. The polyisocyanate composition A) is thus used as reactant in the process of the invention. When reference is made here to "polyisocyanate composition A)", especially to "providing the polyisocyanate composition A)", this means that the polyisocyanate composition A) exists and is used as reactant.

According to the invention, the polyisocyanate composition A) used as reactant in the trimerization is low in monomers (i.e. low in monomeric diisocyanates) and already contains oligomeric polyisocyanates. In one embodiment of the invention, the polyisocyanate composition A) consists entirely or to an extent of at least 80%, 85%, 90%, 95%, 98%, 99% or 99.5% by weight, based in each case on the weight of the polyisocyanate composition A), of oligomeric polyisocyanates. This content of oligomeric polyisocyanates is based on the polyisocyanate composition A), meaning that they are not, for instance, formed as intermediate during the process of the invention but are already present at the start of the reaction in the polyisocyanate composition A) used as reactant.

"Low in monomers" and "low in monomeric diisocyanates" are used synonymously here in relation to the polyisocyanate composition A).

Results of particular practical relevance are established when the polyisocyanate composition A) has a proportion of monomeric diisocyanates in the polyisocyanate composition A) of not more than 20% by weight, especially not more than 15% by weight or not more than 10% by weight, based in each case on the weight of the polyisocyanate composition A). Preferably, the polyisocyanate composition A) has a content of monomeric diisocyanates of not more than 5% by weight, especially not more than 2.0% by weight, more preferably not more than 1.0% by weight, based in each case on the weight of the polyisocyanate composition A). Particularly good results are established when the polymer composition A) is essentially free of monomeric diisocyanates. "Essentially free" means that the content of monomeric diisocyanates is not more than 0.5% by weight, based on the weight of the polyisocyanate composition A).

It is essential to the invention that the polyisocyanate composition A) used is a low-monomer composition. In practice, this can especially be achieved by using, as polyisocyanate composition A), oligomeric polyisocyanates whose preparation involves, after the actual modification reaction, at least one further process step in each case for removal of the unconverted excess monomeric diisocyanates. In a manner of particular practical relevance, this monomer removal can be effected by processes known per se, preferably by thin-film distillation under high vacuum or by extraction with suitable solvents that are inert toward isocyanate groups, for example aliphatic or cycloaliphatic hydrocarbons such as pentane, hexane, heptane, cyclopentane or cyclohexane.

In a preferred embodiment of the invention, the polyisocyanate composition A) of the invention is obtained by modification of monomeric diisocyanates with subsequent removal of unconverted monomers.

The processes described in the prior art for production of polyisocyanurate plastics use very substantially monomeric diisocyanates as reactants, meaning that pure monomeric diisocyanates or monomer-rich polyisocyanate compositions are catalytically trimerized. In contrast, the inventive use or the "provision" of a low-monomer polyisocyanate composition A) already containing oligomeric polyisocyanates surprisingly leads to a much lower volume shrinkage. The lower exothermicity of the inventive reaction additionally allows polyisocyanurate plastics with a high conversion level to be obtained.

Preferably, no monomeric diisocyanate is used in the trimerization reaction of the invention. In a particular embodiment of the invention, however, the polyisocyanate composition A) may contain an extra monomeric diisocyanate. In this context, "extra monomeric diisocyanate" means that it differs from the monomeric diisocyanates which have been used for preparation of the oligomeric polyisocyanates present in the polyisocyanate composition A). Addition of extra monomeric diisocyanate may be advantageous for achievement of special technical effects, for example an exceptional hardness. Results of particular practical relevance are established when the polyisocyanate composition A) has a proportion of extra monomeric diisocyanate in the polyisocyanate composition A) of not more than 20% by weight, especially not more than 15% by weight or not more than 10% by weight, based in each case on the weight of the polyisocyanate composition A). Preferably, the polyisocyanate composition A) has a content of extra monomeric diisocyanate of not more than 5% by weight, especially not more than 2.0% by weight, more preferably not more than 1.0% by weight, based in each case on the weight of the polyisocyanate composition A).

In a further particular embodiment of the process of the invention, the polyisocyanate composition A) may contain monomeric monoisocyanates or monomeric isocyanates having an isocyanate functionality greater than two, i.e. having more than two isocyanate groups per molecule. The addition of monomeric monoisocyanates or monomeric isocyanates having an isocyanate functionality greater than two has been found to be particularly advantageous in order to influence the network density of the polyisocyanurate plastic. Results of particular practical relevance are established when the polyisocyanate composition A) has a proportion of monomeric monoisocyanates or monomeric isocyanates having an isocyanate functionality greater than two in the polyisocyanate composition A) of not more than 20% by weight, especially not more than 15% by weight or not more than 10% by weight, based in each case on the weight of the polyisocyanate composition A). Preferably, the polyisocyanate composition A) has a content of monomeric monoisocyanates or monomeric isocyanates having an isocyanate functionality greater than two of not more than 5% by weight, especially not more than 2.0% by weight, more preferably not more than 1.0% by weight, based in each case on the weight of the polyisocyanate composition A). Preferably, no monomeric monoisocyanate or monomeric isocyanate having an isocyanate functionality greater than two is used in the inventive trimerization reaction.

The low-monomer polyisocyanate composition A) and the oligomeric polyisocyanates present therein are typically obtained by modifying simple aliphatic, cycloaliphatic, araliphatic and/or aromatic monomeric diisocyanates or mixtures of such monomeric diisocyanates.

The oligomeric polyisocyanates may, in accordance with the invention, especially have uretdione, isocyanurate, allophanate, biuret, iminooxadiazinedione and/or oxadiazinetrione structure. In one embodiment of the invention, the oligomeric polyisocyanates have at least one of the following oligomeric structure types or mixtures thereof:

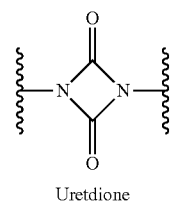

Uretdione

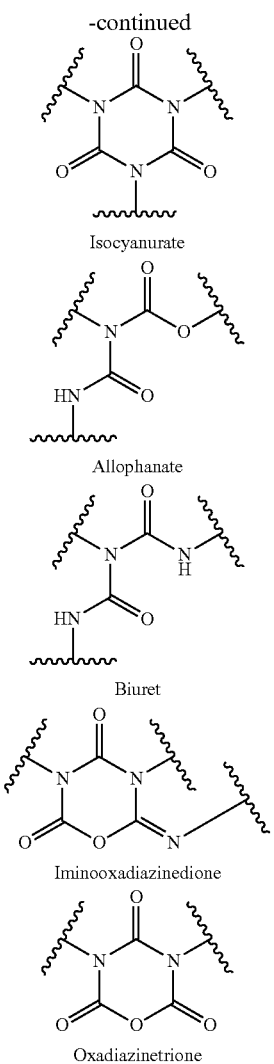

Isocyanurate

Allophanate

Biuret

Iminooxadiazinedione

Oxadiazinetrione

In an especially preferred embodiment of the present invention, the low-monomer polyisocyanate composition A) has at least one structure selected from the group consisting of uretdione, isocyanurate, biuret, iminooxadiazinedione and/or oxadiazinetrione, but is essentially free of allophanate structures. The term "essentially free of allophanate structures" refers to a ratio of isocyanurate groups to allophanate groups of more than 99:1. All other definitions given above with the exception of the allophanate-content also apply to this embodiment.

The study underlying the present invention has surprisingly shown that contrary to the teaching of WO 2015/166983 polyisocyanurate plastics with satisfactory technical properties can be produced from polyisocyanates which do not contain allophanate groups.

It has been found that, surprisingly, it may be advantageous to use oligomeric polyisocyanates which are a mixture of at least two oligomeric polyisocyanates, where the at least two oligomeric polyisocyanates are of different structure. This structure is preferably selected from the group consisting of uretdione, isocyanurate, allophanate, biuret, iminooxadiazinedione and oxadiazinetrione structure, and mixtures thereof. Starting mixtures of this kind, especially compared to trimerization reactions with oligomeric polyisocyanates of just one defined structure, can lead to an effect on the Tg value, which is advantageous for many applications.

Preferably, in the process of the invention, a polyisocyanate composition A) consisting of at least one oligomeric polyisocyanate having biuret, allophanate, isocyanurate and/or iminooxadiazinedione structure and mixtures thereof is used.

In another embodiment, the polyisocyanate composition A) is one which contains only a single defined oligomeric structure, for example exclusively or for the most part isocyanurate structure. In general, as a result of the preparation, however, there are always several different oligomeric structures present alongside one another in the polyisocyanate composition A).

In the context of the present invention, a polyisocyanate composition A) is regarded as a polyisocyanate composition of a single defined oligomeric structure when an oligomeric structure selected from uretdione, isocyanurate, allophanate, biuret, iminooxadiazinedione and/or oxadiazinetrione structure is present to an extent of at least 50 mol %, preferably 60 mol %, more preferably 70 mol %, especially preferably 80 mol %, particularly 90 mol %, based in each case on the sum total of the oligomeric structures from the group consisting of uretdione, isocyanurate, allophanate, biuret, iminooxadiazinedione and oxadiazinetrione present in the polyisocyanate composition A).

In the process of the invention, in a further embodiment, a polyisocyanate composition A) of a single defined oligomeric structure, wherein the oligomeric structure is selected from uretdione, isocyanurate, allophanate, biuret, iminooxadiazinedione and/or oxadiazinetrione structure and is present to an extent of at least 50 mol %, preferably 60 mol %, more preferably 70 mol %, especially preferably 80 mol %, particularly 90 mol %, based in each case on the sum total of the oligomeric structures from the group consisting of uretdione, isocyanurate, allophanate, biuret, iminooxadiazinedione and oxadiazinetrione structure present in the polyisocyanate composition A), is used.

In a further embodiment, the oligomeric polyisocyanates are those having mainly isocyanurate structure, and may contain the abovementioned uretdione, allophanate, biuret, iminooxadiazinedione and/or oxadiazinetrione structure only as by-products. Thus, one embodiment of the invention envisages the use of a polymer composition A) of a single defined oligomeric structure, the oligomeric structure being an isocyanurate structure and being present to an extent of at least 50 mol %, preferably 60 mol %, more preferably 70 mol %, especially preferably 80 mol %, particularly 90 mol %, based in each case on the sum total of the oligomeric structures from the group consisting of uretdione, isocyanurate, allophanate, biuret, iminooxadiazinedione and oxadiazinetrione structure present in the polyisocyanate composition A).

It is likewise possible in accordance with the invention to use oligomeric polyisocyanates having very substantially no isocyanurate structure, and containing mainly at least one of the abovementioned uretdione, allophanate, biuret, iminooxadiazinedione and oxadiazinetrione structure types. In a particular embodiment of the invention, the polyisocyanate composition A) consists to an extent of at least 50 mol %, preferably 60 mol %, more preferably 70 mol %, especially preferably 80 mol %, particularly 90 mol %, based in each case on the sum total of the oligomeric structures from the group consisting of uretdione, isocyanurate, allophanate, biuret, iminooxadiazinedione and oxadiazinetrione structure present in the polyisocyanate composition A), of oligomeric polyisocyanates having a structure type selected from the group consisting of uretdione, allophanate, biuret, iminooxadiazinedione and/or oxadiazinetrione structure.

A further embodiment of the invention envisages the use of a low-isocyanurate polyisocyanate composition A) which, based on the sum total of the oligomeric structures from the group consisting of uretdione, isocyanurate, allophanate, biuret, iminooxadiazinedione and oxadiazinetrione structure present in the polyisocyanate composition A), contains not more than as 50 mol %, preferably not more than as 40 mol %, more preferably not more than as 30 mol %, especially preferably not more than as 20 mol %, 10 mol % or 5 mol % of isocyanurate structures. A further embodiment of the invention envisages the use of a polymer composition A) of a single defined oligomeric structure type, said oligomeric structure type being selected from the group consisting of uretdione, allophanate, biuret, iminooxadiazinedione and/or oxadiazinetrione structure and this structure type being present to an extent of at least 50 mol %, preferably 60 mol %, more preferably 70 mol %, especially preferably 80 mol %, particularly 90 mol %, based on the sum total of the oligomeric structures from the group consisting of uretdione, isocyanurate, allophanate, biuret, iminooxadiazinedione and oxadiazinetrione structure present in the polyisocyanate composition A).

The proportions of uretdione, isocyanurate, allophanate, biuret, iminooxadiazinedione and/or oxadiazinetrione structure in the polyisocyanate composition A) can be determined, for example, by NMR spectroscopy. It is possible here with preference to use $^{13}$C NMR spectroscopy, preferably in proton-decoupled form, since the oligomeric structures mentioned give characteristic signals.

Irrespective of underlying oligomeric structure type (uretdione, isocyanurate, allophanate, biuret, iminooxadiazinedione and/or oxadiazinetrione structure), the oligomeric polyisocyanate composition A) to be used in the process of the invention and/or the oligomeric polyisocyanates present therein preferably have/has a (mean) NCO functionality of 2.0 to 5.0, preferably of 2.3 to 4.5.

Results of particular practical relevance are established when the polyisocyanate composition A) for use in accordance with the invention has a content of isocyanate groups of 8.0% to 28.0% by weight. It has been found to be of particular practical relevance when the polyisocyanate composition A) of the invention has a content of isocyanate groups of 14.0% to 25.0% by weight, based in each case on the weight of the polyisocyanate composition A).

Preparation processes for the oligomeric polyisocyanates having uretdione, isocyanurate, allophanate, biuret, iminooxadiazinedione and/or oxadiazinetrione structure for use in accordance with the invention in the low-monomer polyisocyanate composition A) are described, for example, in J. Prakt. Chem. 336 (1994) 185-200, in DE-A 1 670 666, DE-A 1 954 093, DE-A 2 414 413, DE-A 2 452 532, DE-A 2 641 380, DE-A 3 700 209, DE-A 3 900 053 and DE-A 3 928 503 or in EP-A 0 336 205, EP-A 0 339 396 and EP-A 0 798 299.

In an additional or alternative embodiment of the invention, the polyisocyanate composition A) of the invention is defined in that it contains oligomeric polyisocyanates which have been obtained from monomeric diisocyanates, irrespective of the nature of the modification reaction used, with observation of an oligomerization level of 5% to 45%, preferably 10% to 40%, more preferably 15% to 30%. "Oligomerization level" is understood here to mean the percentage of isocyanate groups originally present in the starting mixture which is consumed during the preparation process to form uretdione, isocyanurate, allophanate, biuret, iminooxadiazinedione and/or oxadiazinetrione structures.

Suitable polyisocyanates for preparation of the polyisocyanate composition A) for use in the process of the invention and the oligomeric polyisocyanates present therein are any desired polyisocyanates obtainable in various ways, for example by phosgenation in the liquid or gas phase or by a phosgene-free route, for example by thermal urethane cleavage. Particularly good results are established when the polyisocyanates are monomeric diisocyanates. Preferred monomeric diisocyanates are those having a molecular weight in the range from 140 to 400 g/mol, having aliphatically, cycloaliphatically, araliphatically and/or aromatically bonded isocyanate groups, for example 1,4-diisocyanatobutane (BDI), 1,5-diisocyanatopentane (PDI), 1,6-diisocyanatohexane (HDI), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane (H12MD1), 1,3- and 1,4-bis(isocyanatomethyl)cyclohexane, bis(isocyanatomethyl)norbornane (NBDI), 4,4'-diisocyanato-3,3'-dimethyldicyclohexylmethane, 4,4'-diisocyanato-3,3',5,5'-tetramethyldicyclohexylmethane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3-dimethyl-5,7-diisocyanatoadamantane, 1,3- and 1,4-bis(isocyanatomethyl)benzene (xylylene diisocyanate; XDI), 1,3- and 1,4-bis(1-isocyanato-1-methylethyl)benzene (TMXDI) and bis(4-(1-isocyanato-1-methylethyl)phenyl) carbonate, 2,4- and 2,6-diisocyanatotoluene (TDI), 2,4'- and 4,4'-diisocyanatodiphenylmethane (MDI), 1,5-diisocyanatonaphthalene and any desired mixtures of such diisocyanates. Further diisocyanates that are likewise suitable can additionally be found, for example, in *Justus Liebigs Annalen der Chemie*, volume 562 (1949) p. 75-136.

Suitable monomeric monoisocyanates which can optionally be used in the polyisocyanate composition A) are, for example, n-butyl isocyanate, n-amyl isocyanate, n-hexyl isocyanate, n-heptyl isocyanate, n-octyl isocyanate, undecyl isocyanate, dodecyl isocyanate, tetradecyl isocyanate, cetyl isocyanate, stearyl isocyanate, cyclopentyl isocyanate, cyclohexyl isocyanate, 3- or 4-methylcyclohexyl isocyanate or any desired mixtures of such monoisocyanates. An example of a monomeric isocyanate having an isocyanate functionality greater than two which can optionally be added to the polyisocyanate composition A) is 4-isocyanatomethyloctane 1,8-diisocyanate (triisocyanatononane; TIN).

In one embodiment of the invention, the polyisocyanate composition A) contains not more than 30% by weight, especially not more than 20% by weight, not more than 15% by weight, not more than 10% by weight, not more than 5% by weight or not more than 1% by weight, based in each case on the weight of the polyisocyanate composition A), of aromatic polyisocyanates. As used here, "aromatic polyisocyanate" means a polyisocyanate having at least one aromatically bonded isocyanate group.

Aromatically bonded isocyanate groups are understood to mean isocyanate groups bonded to an aromatic hydrocarbyl radical.

In a preferred embodiment of the process of the invention, a polyisocyanate composition A) having exclusively aliphatically and/or cycloaliphatically bonded isocyanate groups is used.

Aliphatically and cycloaliphatically bonded isocyanate groups are understood to mean isocyanate groups bonded, respectively, to an aliphatic and cycloaliphatic hydrocarbyl radical.

In another preferred embodiment of the process of the invention, a polyisocyanate composition A) consisting of or comprising one or more oligomeric polyisocyanates is used, where the one or more oligomeric polyisocyanates has/have exclusively aliphatically and/or cycloaliphatic bonded isocyanate groups.

In a further embodiment of the invention, the polyisocyanate composition A) consists to an extent of at least 70%, 80%, 85%, 90%, 95%, 98% or 99% by weight, based in each case on the weight of the polyisocyanate composition A), of polyisocyanates having exclusively aliphatically and/or cycloaliphatically bonded isocyanate groups. Practical experiments have shown that particularly good results can be achieved with polyisocyanate compositions A) in which the oligomeric polyisocyanates present therein have exclusively aliphatically and/or cycloaliphatically bonded isocyanate groups.

In a particularly preferred embodiment of the process of the invention, a polyisocyanate composition A) is used which consists of or comprises one or more oligomeric polyisocyanates, where the one or more oligomeric polyisocyanates is/are based on 1,5-diisocyanatopentane (PDI), 1,6-diisocyanatohexane (HDI), isophorone diisocyanate (IPDI) or 4,4'-diisocyanatodicyclohexylmethane (H12MDI) or mixtures thereof.

The polyisocyanurates of the invention are obtainable by catalytic trimerization in accordance with the process of the invention. "Catalytic" here means in the presence of a suitable catalyst B).

Suitable catalysts B) for the process of the invention are in principle any compounds which accelerate the trimerization of isocyanate groups to isocyanurate structures. Since isocyanurate formation, depending on the catalyst used, is frequently accompanied by side reactions, for example dimerization to give uretdione structures or trimerization to form iminooxadiazinediones (called asymmetric trimers), and, in the presence of urethane groups in the starting polyisocyanate, by allophanatization reactions, the term "trimerization" in the context of the present invention is also to be used synonymously for these reactions that proceed additionally.

In a particular embodiment, however, trimerization means that predominantly cyclotrimerizations of at least 50%, preferably at least 60%, more preferably at least 70% and especially at least 80% of isocyanate groups present in the polyisocyanate composition A) to give isocyanurate structural units are catalysed. However, side reactions, especially those to give uretdione, allophanate and/or iminooxadiazinedione structures, typically occur and can even be used in a controlled manner in order to advantageously affect, for example, the Tg value of the polyisocyanurate plastic obtained.

Suitable catalysts B) for the process of the invention are, for example, simple tertiary amines, for example triethylamine, tributylamine, N,N-dimethylaniline, N-ethylpiperidine or N,N'-dimethylpiperazine. Suitable catalysts are also the tertiary hydroxyalkylamines described in GB 2 221 465, for example triethanolamine, N-methyldiethanolamine, dimethylethanolamine, N-isopropyldiethanolamine and 1-(2-hydroxyethyl)pyrrolidine, or the catalyst systems that are known from GB 2 222 161 and consist of mixtures of tertiary bicyclic amines, for example DBU, with simple low molecular weight aliphatic alcohols.

Likewise suitable as trimerization catalysts B) for the process of the invention are a multitude of different metal compounds. Suitable examples are the octoates and naphthenates of manganese, iron, cobalt, nickel, copper, zinc, zirconium, cerium or lead that are described as catalysts in DE-A 3 240 613, or mixtures thereof with acetates of lithium, sodium, potassium, calcium or barium, the sodium and potassium salts of linear or branched alkanecarboxylic acids having up to 10 carbon atoms that are known from DE-A 3 219 608, for example of propionic acid, butyric acid, valeric acid, caproic acid, heptanoic acid, caprylic acid, pelargonic acid, capric acid and undecyl acid, the alkali metal or alkaline earth metal salts of aliphatic, cycloaliphatic or aromatic mono- and polycarboxylic acids having 2 to 20 carbon atoms that are known from EP-A 0 100 129, for example sodium or potassium benzoate, the alkali metal phenoxides known from GB-A 1 391 066 and GB-A 1 386 399, for example sodium or potassium phenoxide, the alkali metal and alkaline earth metal oxides, hydroxides, carbonates, alkoxides and phenoxides known from GB 809 809, alkali metal salts of enolizable compounds and metal salts of weak aliphatic or cycloaliphatic carboxylic acids, for example sodium methoxide, sodium acetate, potassium acetate, sodium acetoacetate, lead 2-ethylhexanoate and lead naphthenate, the basic alkali metal compounds complexed with crown ethers or polyether alcohols that are known from EP-A 0 056 158 and EP-A 0 056 159, for example complexed sodium or potassium carboxylates, the pyrrolidinone-potassium salt known from EP-A 0 033 581, the mono- or polynuclear complex of titanium, zirconium and/or hafnium known from application EP 13196508.9, for example zirconium tetra-n butoxide, zirconium tetra-2-ethylhexanoate and zirconium tetra-2-ethylhexoxide, and tin compounds of the type described in *European Polymer Journal, vol.* 16, 147-148 (1979), for example dibutyltin dichloride, diphenyltin dichloride, triphenylstannanol, tributyltin acetate, tributyltin oxide, tin octoate, dibutyl(dimethoxy)stannane and tributyltin imidazolate.

Further trimerization catalysts B) suitable for the process of the invention are, for example, the quaternary ammonium hydroxides known from DE-A 1 667 309, EP-A 0 013 880 and EP-A 0 047 452, for example tetraethylammonium hydroxide, trimethylbenzylammonium hydroxide, N,N-dimethyl-N-dodecyl-N-(2-hydroxyethyl)ammonium hydroxide, N-(2-hydroxyethyl)-N,N-dimethyl-N-(2,2'-dihydroxymethylbutyl)ammonium hydroxide and 1-(2-hydroxyethyl)-1,4-diazabicyclo[2.2.2]octane hydroxide (monoadduct of ethylene oxide and water with 1,4-diazabicyclo[2.2.2]octane), the quaternary hydroxyalkylammonium hydroxides known from EP-A 37 65 or EP-A 10 589, for example N,N,N-trimethyl-N-(2-hydroxyethyl)ammonium hydroxide, the trialkylhydroxylalkylammonium carboxylates that are known from DE-A 2631733, EP-A 0 671 426, EP-A 1 599 526 and U.S. Pat. No. 4,789,705, for example N,N,N-trimethyl-N-2-hydroxypropylammonium p-tert-butylbenzoate and N,N,N-trimethyl-N-2-hydroxypropylammonium 2-ethylhexanoate, the quaternary benzylammonium carboxylates known from EP-A 1 229 016, such as N-benzyl-N,N-dimethyl-N-ethylammonium pivalate, N-benzyl-N,N-dimethyl-N-ethylammonium 2-ethylhexanoate, N-benzyl-N,N,N-tributylammonium 2-ethylhexanoate, N,N-dimethyl-N-ethyl-N-(4-methoxybenzyl)ammonium 2-ethylhexanoate or N,N,N-tributyl-N-(4-methoxybenzyl) ammonium pivalate, the tetrasubstituted ammonium α-hydroxycarboxylates known from WO 2005/087828, for example tetramethylammonium lactate, the quaternary ammonium or phosphonium fluorides known from EP-A 0

339 396, EP-A 0 379 914 and EP-A 0 443 167, for example N-methyl-N,N,N-trialkylammonium fluorides with $C_8$-$C_{10}$-alkyl radicals, N,N,N,N-tetra-n-butylammonium fluoride, N,N,N-trimethyl-N-benzylammonium fluoride, tetramethylphosphonium fluoride, tetraethylphosphonium fluoride or tetra-n-butylphosphonium fluoride, the quaternary ammonium and phosphonium polyfluorides known from EP-A 0 798 299, EP-A 0 896 009 and EP-A 0 962 455, for example benzyltrimethylammonium hydrogen polyfluoride, the tetraalkylammonium alkylcarbonates which are known from EP-A 0 668 271 and are obtainable by reaction of tertiary amines with dialkyl carbonates, or betaine-structured quaternary ammonioalkyl carbonates, the quaternary ammonium hydrogencarbonates known from WO 1999/023128, such as choline bicarbonate, the quaternary ammonium salts which are known from EP 0 102 482 and are obtainable from tertiary amines and alkylating esters of phosphorus acids, examples of such salts being reaction products of triethylamine, DABCO or N-methylmorpholine with dimethyl methanephosphonate, or the tetrasubstituted ammonium salts of lactams that are known from WO 2013/167404, for example trioctylammonium caprolactamate or dodecyltrimethylammonium caprolactamate.

Further trimerization catalysts suitable for the process of the invention can be found, for example, in J. H. Saunders and K. C. Frisch, Polyurethanes Chemistry and Technology, p. 94 ff. (1962) and the literature cited therein.

The catalysts B) can be used in the process of the invention either individually or in the form of any desired mixtures with one another.

Preferred catalysts B) are metal compounds of the aforementioned type, especially carboxylates and alkoxides of alkali metals, alkaline earth metals or zirconium, and organic tin compounds of the type mentioned.

Particularly preferred trimerization catalysts B) are sodium and potassium salts of aliphatic carboxylic acids having 2 to 20 carbon atoms, and aliphatically substituted tin compounds.

Very particularly preferred trimerization catalysts B) for the process of the invention are potassium acetate, tin octoate and/or tributyltin oxide.

In the process of the invention, the trimerization catalyst B) is generally used in a concentration based on the amount of the polyisocyanate composition A) used of 0.0005% to 5.0% by weight, preferably of 0.0010% to 2.0% by weight and more preferably of 0.0015% to 1.0% by weight.

The trimerization catalysts B) that are used in the process of the invention generally have sufficient solubility in the polyisocyanate composition A) in the amounts that are required for initiation of the oligomerization reaction. The catalyst B) is therefore preferably added to the polyisocyanate composition A) in neat form.

Optionally, however, the catalysts B) can also be used dissolved in a suitable organic solvent to improve their incorporability. The dilution level of the catalyst solutions can be freely selected within a very wide range. Catalytically active catalyst solutions are typically those of a concentration over and above about 0.01% by weight.

Suitable catalyst solvents are, for example, solvents that are inert toward isocyanate groups, for example hexane, toluene, xylene, chlorobenzene, ethyl acetate, butyl acetate, diethylene glycol dimethyl ether, dipropylene glycol dimethyl ether, ethylene glycol monomethyl or monoethyl ether acetate, diethylene glycol ethyl and butyl ether acetate, propylene glycol monomethyl ether acetate, 1-methoxyprop-2-yl acetate, 3-methoxy-n-butyl acetate, propylene glycol diacetate, acetone, methyl ethyl ketone, methyl isobutyl ketone, cyclohexanone, lactones such as β-propiolactone, γ-butyrolactone, ε-caprolactone and ε-methylcaprolactone, but also solvents such as N-methylpyrrolidone and N-methylcaprolactam, 1,2-propylene carbonate, methylene chloride, dimethyl sulphoxide, triethyl phosphate or any desired mixtures of such solvents.

If catalyst solvents are used in the process of the invention, preference is given to using catalyst solvents which bear groups reactive toward isocyanates and can be incorporated into the polyisocyanurate plastic. Examples of such solvents are mono- and polyhydric simple alcohols, for example methanol, ethanol, n-propanol, isopropanol, n-butanol, n-hexanol, 2-ethyl-1-hexanol, ethylene glycol, propylene glycol, the isomeric butanediols, 2-ethylhexane-1,3-diol or glycerol; ether alcohols, for example 1-methoxy-2-propanol, 3-ethyl-3-hydroxymethyloxetane, tetrahydrofurfuryl alcohol, ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, diethylene glycol, dipropylene glycol or else liquid higher molecular weight polyethylene glycols, polypropylene glycols, mixed polyethylene/polypropylene glycols and the monoalkyl ethers thereof; ester alcohols, for example ethylene glycol monoacetate, propylene glycol monolaurate, glycerol mono- and diacetate, glycerol monobutyrate or 2,2,4-trimethylpentane-1,3-diol monoisobutyrate; unsaturated alcohols, for example allyl alcohol, 1,1-dimethyl allyl alcohol or oleyl alcohol; araliphatic alcohols, for example benzyl alcohol; N-monosubstituted amides, for example N-methylformamide, N-methylacetamide, cyanoacetamide or 2-pyrrolidone, or any desired mixtures of such solvents.

The polyisocyanurate plastics obtainable in accordance with the process of the invention even as such, i.e. without addition of appropriate auxiliaries and additives C), feature very good light stability. Nevertheless, it is optionally possible to use standard auxiliaries and/or additives C) as well in the production thereof, for example standard fillers, UV stabilizers, antioxidants, mould release agents, water scavengers, slip additives, defoamers, levelling agents, rheology additives, flame retardants and/or pigments. These auxiliaries and/or additives C), excluding fillers and flame retardants, are typically present in the polyisocyanurate plastic in an amount of less than 10% by weight, preferably less than 5% by weight, more preferably up to 3% by weight, based on the polyisocyanate composition A). Flame retardants are typically present in the polyisocyanurate plastic in amounts of not more than 70% by weight, preferably not more than 50% by weight and more preferably not more than 30% by weight, calculated as the total amount of flame retardants used, based on the polyisocyanate composition A).

Suitable fillers $C_w$) are, for example $AlOH_3$, $CaCO_3$, metal pigments such as $TiO_2$ and further known standard fillers. These fillers $C_w$) are preferably used in amounts of not more than 70% by weight, preferably not more than 50% by weight and more preferably not more than 30% by weight, calculated as the total amount of fillers used, based on the polyisocyanate composition A). In an especially preferred embodiment, the invention relates to a polyisocyanurate plastic which is obtainable by catalytic trimerization of a polyisocyanate composition A) which contains (1.) oligomeric polyisocyanates and (2.) is low in monomeric diisocyanates, "low in monomeric diisocyanates" meaning that the polyisocyanate composition A) has a content of monomeric diisocyanates of at most 20% by weight, wherein the polyisocyanurate plast contains at least one filler $C_w$) as defined above.

Suitable UV stabilizers $C_x$) may preferably be selected from the group consisting of piperidine derivatives, for example 4-benzoyloxy-2,2,6,6-tetramethylpiperidine, 4-benzoyloxy-1,2,2,6,6-pentamethylpiperidine, bis(2,2,6,6-tetramethyl-4-piperidyl) sebacate, bis(1,2,2,6,6-pentamethyl-1-4-piperidinyl) sebacate, bis(2,2,6,6-tetramethyl-4-piperidyl) suberate, bis(2,2,6,6-tetramethyl-4-piperidyl) dodecanedioate; benzophenone derivates, for example 2,4-dihydroxy-, 2-hydroxy-4-methoxy-, 2-hydroxy-4-octoxy-, 2-hydroxy-4-dodecyloxy- or 2,2'-dihydroxy-4-dodecyloxy-benzophenone; benzotriazole derivatives, for example 2-(2H-benzotriazol-2-yl)-4,6-di-tert-pentylphenol, 2-(2H-benzotriazol-2-yl)-6-dodecyl-4-methylphenol, 2-(2H-benzotriazol-2-yl)-4,6-bis(1-methyl-1-phenylethyl)phenol, 2-(5-chloro-2H-benzotriazol-2-yl)-6-(1,1-dimethylethyl)-4-methylphenol, 2-(2H-benzotriazol-2-yl)-4-(1,1,3,3-tetramethylbutyl)phenol, 2-(2H-benzotriazol-2-yl)-6-(1-methyl-1-phenylethyl)-4-(1,1,3,3-tetramethylbutyl)phenol, isooctyl 3-(3-(2H-benzotriazol-2-yl)-5-(1,1-dimethylethyl)-4-hydroxyphenylpropionate), 2-(2H-benzotriazol-2-yl)-4,6-bis(1,1-dimethylethyl)phenol, 2-(2H-benzotriazol-2-yl)-4,6-bis(1-methyl-1-phenylethyl)phenol, 2-(5-chloro-2H-benzotriazol-2-yl)-4,6-bis(1,1-dimethylethyl)phenol; oxalanilides, for example 2-ethyl-2'-ethoxy- or 4-methyl-4'-methoxyoxalanilide; salicylic esters, for example phenyl salicylate, 4-tert-butylphenyl salicylate, 4-tert-octylphenyl salicylate; cinnamic ester derivatives, for example methyl α-cyano-β-methyl-4-methoxycinnamate, butyl α-cyano-β-methyl-4-methoxycinnamate, ethyl α-cyano-β-phenylcinnamate, isooctyl α-cyano-β-phenylcinnamate; and malonic ester derivatives, such as dimethyl 4-methoxybenzylidenemalonate, diethyl 4-methoxybenzylidenemalonate, dimethyl 4 butoxybenzylidenemalonate. These preferred light stabilizers can be used either individually or in any desired combinations with one another.

Particularly preferred UV stabilizers $C_x$) for the polyisocyanurate plastics producible in accordance with the invention are those which fully absorb radiation of wavelength<400 nm. These include, for example, the benzotriazole derivatives mentioned. Especially preferred UV stabilizers are 2-(5-chloro-2H-benzotriazol-2-yl)-6-(1,1-dimethylethyl)-4-methylphenol, 2-(2H-benzotriazol-2-yl)-4-(1,1,3,3-tetramethylbutyl)phenol and/or 2-(5-chloro-2H-benzotriazol-2-yl)-4,6-bis(1,1-dimethylethyl)phenol.

It is optionally possible to add one or more of the UV stabilizers $C_x$) mentioned by way of example to the polyisocyanate composition A), preferably in amounts of 0.001% to 3.0% by weight, more preferably 0.01% to 2% by weight, calculated as the total amount of UV stabilizers used, based on the total weight of the polyisocyanate composition A).

In an especially preferred embodiment, the invention relates to a polyisocyanurate plastic which is obtainable by catalytic trimerization of a polyisocyanate composition A) which contains (1.) oligomeric polyisocyanates and (2.) is low in monomeric diisocyanates, "low in monomeric diisocyanates" meaning that the polyisocyanate composition A) has a content of monomeric diisocyanates of at most 20% by weight, wherein the polyisocyanurate plast contains at least one UV stabilizer $C_x$) as defined above.

Suitable antioxidants $C_y$) are preferably sterically hindered phenols, which may be selected preferably from the group consisting of 2,6-di-tert-butyl-4-methylphenol (ionol), pentaerythritol tetrakis(3-(3,5-di-tert-butyl-4-hydroxyphenyl)propionate), octadecyl 3-(3,5-di-tert-butyl-4-hydroxyphenyl)propionate, triethylene glycol bis(3-tert-butyl-4-hydroxy-5-methylphenyl)propionate, 2,2'-thiobis(4-methyl-6-tert-butylphenol) and 2,2'-thiodiethyl bis[3-(3,5-di-tert-butyl-4-hydroxyphenyl)propionate]. If required, they can be used either individually or in any desired combinations with one another.

These antioxidants $C_y$) are preferably used in amounts of 0.01% to 3.0% by weight, more preferably 0.02% to 2.0% by weight, calculated as the total amount of antioxidants used, based on the polyisocyanate composition A).

In an especially preferred embodiment, the invention relates to a polyisocyanurate plastic which is obtainable by catalytic trimerization of a polyisocyanate composition A) which contains (1.) oligomeric polyisocyanates and (2.) is low in monomeric diisocyanates, "low in monomeric diisocyanates" meaning that the polyisocyanate composition A) has a content of monomeric diisocyanates of at most 20% by weight, wherein the polyisocyanurate plast contains at least one antioxidant $C_y$) as defined above.

Apart from the small amounts of any catalyst solvents for use in addition, the process of the invention can be conducted without solvent. More particularly, in the case of the inventive use for production of coatings or films, the polyisocyanate component can optionally alternatively be diluted with organic solvents in order to reduce the processing viscosity. Solvents suitable for this purpose are, for example, the catalyst solvents that are inert toward isocyanate groups and have already been described above.

In the case of the inventive use for production of films, semi-finished products or mouldings, further auxiliaries and additives C) added, finally, may also be internal mould release agents $C_z$).

These are preferably the nonionic surfactants containing perfluoroalkyl or polysiloxane units that are known as mould release agents, quaternary alkylammonium salts, for example trimethylethylammonium chloride, trimethylstearylammonium chloride, dimethylethylcetylammonium chloride, triethyldodecylammonium chloride, trioctylmethylammonium chloride and diethylcyclohexyldodecylammonium chloride, acidic monoalkyl and dialkyl phosphates having 2 to 18 carbon atoms in the alkyl radical, for example ethyl phosphate, diethyl phosphate, isopropyl phosphate, diisopropyl phosphate, butyl phosphate, dibutyl phosphate, octyl phosphate, dioctyl phosphate, isodecyl phosphate, diisodecyl phosphate, dodecyl phosphate, didodecyl phosphate, tridecanol phosphate, bis(tridecanol) phosphate, stearyl phosphate, distearyl phosphate, and any desired mixtures of such mould release agents.

Particularly preferred mould release agents $C_z$) are the acidic mono- and dialkyl phosphates mentioned, most preferably those having 8 to 12 carbon atoms in the alkyl radical.

Internal mould release agents $C_z$) are used in the process of the invention, if appropriate, preferably in amounts of 0.01% to 3.0% by weight, more preferably 0.02% to 2.0% by weight, calculated as the total amount of internal mould release agent used, based on the polyisocyanate composition A).

In an especially preferred embodiment, the present invention relates to relates to a polyisocyanurate plastic which is obtainable by catalytic trimerization of a polyisocyanate composition A) which contains (1.) oligomeric polyisocyanates and (2.) is low in monomeric diisocyanates, "low in monomeric diisocyanates" meaning that the polyisocyanate composition A) has a content of monomeric diisocyanates of at most 20% by weight and wherein the polyisoxyanurate plastic contains at least one mould. release agent $C_z$) as defined above.

In one embodiment of the process of the invention, a trimerization catalyst B) or a mixture of different trimerization catalysts B) is added to the polyisocyanate composition A) described, optionally under inert gas, for example nitrogen, and optionally with additional use of the aforementioned solvents and auxiliaries and additives C), and mixed in homogeneously with the aid of a suitable mixing unit. The addition of catalyst B) and any solvent and auxiliaries and additives C) for additional use can take place in any sequence, successively or in a mixture, in the above-specified amounts and generally at a temperature of 0 to 100° C., preferably of 15 to 80° C., more preferably of 20 to 60° C.

The application of the catalysed reaction mixtures thus obtained can be effected by different methods known per se according to the end use. For production of films or coatings, for example paints, a mixture of catalyst B) and polyisocyanate composition A) can be applied, for example, by spraying, spreading, dipping or flow-coating or with the aid of brushes, rollers or doctor blades, in one or more layers to any desired substrates, for example metal, wood, glass, stone, ceramic materials, concrete, hard and flexible plastics, textiles, leather and paper, which may optionally also be provided with standard primers prior to the coating.

For production of solid bodies, for example semi-finished products or mouldings, the mixture of catalyst B) and polyisocyanate composition A) may be introduced into open or closed moulds, for example by simple manual pouring, or with the aid of suitable machinery, for example the low-pressure or high-pressure machinery which is standard in polyurethane technology.

Subsequently, the trimerization reaction can be started by heating, for example, the coated substrates or filled moulds, the optimal reaction temperature, depending on the catalyst chosen in each case, being from 20 to 250° C., preferably from 40 to 200° C., more preferably from 60 to 150° C. The reaction temperature can be kept constant within the range specified over the entire curing operation to give the polyisocyanurate, or else be heated, for example over the course of several hours, in a linear or stepwise manner up to a temperature of greater than 80° C., preferably greater than 100° C., for example up to 130° C. When "reaction temperature" is mentioned here, this means the ambient temperature.

Depending on the catalyst B) chosen and the reaction temperature chosen, the trimerization reaction is very substantially complete, as defined below, after a period of less than one minute up to several hours or only after a few days. The progress of the reaction can initially still be monitored by titrimetric determination of the NCO content, but gelation and solidification of the reaction mixture sets in rapidly with advancing conversion, which makes wet-chemical analysis methods impossible. The further conversion of isocyanate groups can then only be monitored by spectroscopic methods, for example by IR spectroscopy with reference to the intensity of the isocyanate band at about 2270 $cm^{-1}$.

The polyisocyanurate plastics of the invention are preferably polyisocyanurates with high conversion, i.e. those in which the trimerization reaction to give polyisocyanurate structures is very substantially complete. A trimerization reaction to give polyisocyanurate structures can be regarded as "very substantially complete" in the context of the present invention when at least 80%, preferably at least 90% and more preferably at least 95% of the free isocyanate groups originally present in the polyisocyanate composition A) have reacted. In other words, preferably only at most 20%, at most 10% and more preferably at most 5% of the isocyanate groups originally present in the polyisocyanate composition A) are present in the polyisocyanurate plastic of the invention. This can be achieved by continuing the catalytic trimerization in the process of the invention at least up to a conversion level at which only, for example, at most 20% of isocyanate groups originally present in the polyisocyanate composition A) are present, such that a polyisocyanurate with high conversion is obtained. The percentage of isocyanate groups still present can be determined by a comparison of the content of isocyanate groups in % by weight in the original polyisocyanate composition A) with the content of isocyanate groups in % by weight in the reaction product, for example by the aforementioned comparison of the intensity of the isocyanate band at about 2270 $cm^{-1}$ by means of IR spectroscopy.

The process of the invention affords transparent, yellowing-stable polyisocyanurate plastics which, according to the type of starting polyisocyanate used, as well as isocyanurate structures, optionally contain further oligomeric structures and are notable for excellent thermal stabilities.

The process of the invention enables synthesis, in a simple manner, by suitable selection of starting polyisocyanates of different oligomeric structures, of polyisocyanurate plastics having different properties, for example different degrees of hardness, mechanical properties or glass transition temperatures.

In contrast with polyisocyanurate plastics which have been produced proceeding from monomeric diisocyanates, for example monomeric HDI, the process products of the invention feature considerably lower volume shrinkage during curing, for which reason they are especially suitable for production of ultrahigh-precision mouldings. The comparatively low heat of reaction released also permits the problem-free production of solid large-volume mouldings.

The invention is elucidated in detail hereinafter by examples.

EXAMPLES

All percentages are based on weight, unless stated otherwise.

The NCO contents were determined by titrimetric means to DIN EN ISO 11909.

The residual monomer contents were measured to DIN EN ISO 10283 by gas chromatography with an internal standard.

All the viscosity measurements were made with a Physica MCR 51 rheometer from Anton Paar Germany GmbH (DE) to DIN EN ISO 3219.

The densities of the starting polyisocyanates were determined to DIN EN ISO 2811, and those of the cured polyisocyanurate plastics to DIN EN ISO 1183-1.

The contents (mol %) of the uretdione, isocyanurate, allophanate, biuret, iminooxadiazinedione and/or oxadiazinetrione structures present in the starting polyisocyanates were calculated from the integrals of proton-decoupled $^{13}C$ NMR spectra (recorded on a Bruker DPX-400 instrument) and are each based on the sum total of uretdione, isocyanurate, allophanate, biuret, iminooxadiazinedione and/or oxadiazinetrione structures present. In the case of HDI polyisocyanates, the individual structural elements have the following chemical shifts (in ppm): uretdione: 157.1; isocyanurate: 148.4; allophanate: 155.7 and 153.8, biuret: 155.5; iminooxadiazinedione: 147.8, 144.3 and 135.3; oxadiazinetrione: 147.8 and 143.9.

The glass transition temperature $T_g$ was determined by means of DSC (differential scanning calorimetry) with a Mettler DSC 12E (Mettler Toledo GmbH, Giessen, Germany) in accordance with DIN EN 61006. Calibration was effected via the melt onset temperature of indium and lead.

10 mg of substance were weighed out in standard capsules. The measurement was effected by three heating runs from −50° C. to +200° C. at a heating rate of 20 K/min with subsequent cooling at a cooling rate of 320 K/min. Cooling was effected by means of liquid nitrogen. The purge gas used was nitrogen. The values reported in the table below are each based on the evaluation of the 1st heating curve, since changes in the sample in the measurement process at high temperatures are possible in the reactive systems being examined as a result of the thermal stress in the DSC. The glass transition temperature $T_g$ determined was the temperature at half the height of a glass transition step.

Shore hardnesses were measured to DIN 53505 with the aid of a Zwick 3100 Shore hardness tester (from Zwick, Germany).

IR spectra were recorded on a Spectrum 2 FT-IR spectrometer from Perkin Elmer, Inc. equipped with an ATR unit.

Starting Compounds

Starting Polyisocyanate A1)

HDI polyisocyanate containing isocyanurate groups, prepared in accordance with Example 11 of EP-A 330 966, with the alteration that the catalyst solvent used was 2-ethylhexanol rather than 2-ethylhexane-1,3-diol. The reaction was stopped at an NCO content of the crude mixture of 42% by adding dibutyl phosphate. Subsequently, unconverted HDI was removed by thin-film distillation at a temperature of 130° C. and a pressure of 0.2 mbar.

NCO content: 23.0%
NCO functionality: 3.2
Monomeric HDI: 0.1%
Viscosity (23° C.): 1200 mPas
Density (20° C.): 1.17 g/cm³
Distribution of the oligomeric structure types:
Isocyanurate: 89.7 mol %
Iminooxadiazinedione 2.5 mol %
Uretdione 2.7 mol %
Allophanate: 5.1 mol %

Starting Polyisocyanate A2)

HDI polyisocyanate containing isocyanurate and iminooxadiazinedione groups, prepared in accordance with Example 4 of EP-A0 962 455, by trimerization of HDI using a 50% solution of tetrabutylphosphonium hydrogendifluoride in isopropanol/methanol (2:1) as catalyst. The reaction was stopped at an NCO content of the crude mixture of 43% by adding dibutyl phosphate. Subsequently, unconverted HDI was removed by thin-film distillation at a temperature of 130° C. and a pressure of 0.2 mbar.

NCO content: 23.4%
NCO functionality: 3.2
Monomeric HDI: 0.2%
Viscosity (23° C.): 700 mPas
Density (20° C.): 1.15 g/cm³
Distribution of the oligomeric structure types:
Isocyanurate: 49.9 mol %
Iminooxadiazinedione 45.3 mol %
Uretdione 4.8 mol %
Allophanate: 0.0 mol %

Starting Polyisocyanate A3)

HDI polyisocyanate containing isocyanurate and uretdione groups, prepared by tributylphosphine-catalysed oligomerization in accordance with Example 1a) of EP-A 0 377 177, with the alteration that no 2,2,4-trimethylpentane-1,3-diol was used. The reaction was stopped at an NCO content of 42%, and unconverted HDI was removed by thin-film distillation at a temperature of 130° C. and a pressure of 0.2 mbar.

NCO content: 22.7%
NCO functionality: 2.2
Monomeric HDI: 0.3%
Viscosity (23° C.): 90 mPas
Density (20° C.): 1.13 g/cm³
Distribution of the oligomeric structure types:
Isocyanurate: 15.6 mol %
Iminooxadiazinedione 6.3 mol %
Uretdione 78.1 mol %
Allophanate: 0.0 mol %

Starting Polyisocyanate A4)

HDI polyisocyanate containing biuret groups, prepared in accordance with the process of EP-A 0 150 769 by reacting 8.2 mol of HDI with 1.0 mol of water in the presence of 0.05 mol of pivalic anhydride at a temperature of 125° C. On attainment of an NCO content of 36.6%, unconverted monomeric HDI was removed together with pivalic anhydride by thin-film distillation at a temperature of 130° C. and a pressure of 0.2 mbar.

NCO content: 23.0%
NCO functionality: 3.2
Monomeric HDI: 0.4%
Viscosity (23° C.): 2500 mPas
Density (20° C.): 1.13 g/cm³
Distribution of the oligomeric structure types:
Biuret: 87.7 mol %
Uretdione 12.3 mol %
Allophanate: 0.0 mol %

Starting Polyisocyanate A5)

HDI polyisocyanate containing allophanate groups, prepared by reaction of 12.5 mol of HDI with 1.0 mol of butane-1,3-diol at a temperature of 105° C. in the presence of 800 ppm of a 5% solution of zinc 2-ethylhexanoate in 2-ethylhexanol as allophanatization catalyst. On attainment of an NCO content of 40.3%, the reaction was stopped by adding 800 ppm of a 5% solution of isophthaloyl dichloride in HDI, and unconverted HDI was removed by thin-film distillation at a temperature of 130° C. and a pressure of 0.2 mbar.

NCO content: 23.0%
NCO functionality: 4.4
Monomeric HDI: 0.2%
Viscosity (23° C.): 4900 mPas
Density (20° C.): 1.12 g/cm³
Distribution of the oligomeric structure types:
Isocyanurate: 3.7 mol %
Uretdione: 3.7 mol %
Allophanate: 92.6 mol %

Starting Polyisocyanate A6)

HDI polyisocyanate containing allophanate and isocyanurate groups, prepared according to Example 1 of EP-A 496 208.

NCO content: 19.8%
NCO functionality: 2.5
Monomeric HDI: 0.3%
Viscosity (23° C.): 570 mPas
Density (20° C.): 1.11 g/cm³
Distribution of the oligomeric structure types:
Isocyanurate: 33.1 mol %
Allophanate: 66.9 mol %

Starting Polyisocyanate A7

The starting isocyanate A1 was distilled to yield a fraction with >99% Polyisocyanurate Trimer of HDI according to $^{13}$C NMR spectroscopy. NCO content: 24.8%
NCO functionality: 3.0
Monomeric HDI: <0.1%
Viscosity (23° C.): 700 mPas
Density (20° C.): 1.17 g/cm³

Distribution of the oligomeric structure types:
Isocyanurate: 99.2 mol %
Iminooxadiazinedione+Uretdione+Allophanate<1 mol %

Example 1 (Inventive)

25 g of the starting polyisocyanate A1) were weighed together with 0.4 g of tin(II) octoate into a polypropylene cup and homogenized with the aid of a Speed-Mixer DAC 150 FVZ (from Hauschild, Germany) at 3500 rpm for 1 min. The closed polypropylene cup was heated in a drying cabinet to 80° C. for 5 h and then heated to 120° C. for 2 h. The specimen was demoulded and heat-treated at 140° C. for a further 2 h.

A transparent polyisocyanurate plastic having the following characteristic data was obtained:
Tg: 127.7° C.
Shore D hardness: 83
Density (20° C.): 1.24 g/cm$^3$
Volume shrinkage: 5.6%

By IR spectroscopy, no isocyanate groups (band at 2270 cm$^{-1}$) were detectable any longer.

Example 2 (Comparative)

25 g of HDI (density: 1.05 g/cm$^3$) were weighed together with 0.4 g of tin(II) octoate into a polypropylene cup and homogenized with the aid of a Speed-Mixer DAC 150 FVZ (from Hauschild, Germany) at 3500 rpm for 1 min. The closed polypropylene cup was heated in a drying cabinet to 80° C. for 5 h and then heated to 120° C. for 2 h. The specimen was demoulded and heat-treated at 140° C. for a further 2 h.

A transparent polyisocyanurate plastic having the following characteristic data was obtained:
Tg: 125.4° C.
Shore D hardness: 79
Density (20° C.): 1.24 g/cm$^3$
Volume shrinkage: 15.3%

By IR spectroscopy, no isocyanate groups (band at 2270 cm$^{-1}$) were detectable any longer.

The comparison shows that the polyisocyanurate plastic produced in accordance with the invention using the polyisocyanate A1) from Example 1, under the same trimerization conditions, exhibits considerably lower volume shrinkage than the polyisocyanurate obtained proceeding from monomeric HDI.

Examples 3 to 7 (Inventive)

By the method described in Example 1, 25 g of each of the starting polyisocyanates A2) to A6) were trimerized with 0.4 g of tin(II) octoate to give polyisocyanurate plastics.

In none of the products obtained were isocyanate groups (band at 2270 cm$^{-1}$) still detectable by IR spectroscopy.

Example 8 (Inventive)

100 g of the starting polyisocyanate are weighed into a polypropylene cup together with a catalyst mixture consisting of 0.177 g of potassium acetate, 0.475 g of [18]crown-6 and 3.115 g of diethylene glycol, and homogenized at 2750 rpm with the aid of a Speed-Mixer DAC 150 FVZ (from Hauschild, Germany) for 1 min. 8 g of the contents of the polypropylene cup are weighed into an aluminium dish of diameter 6.3 cm and depth 1 cm which, for better demoulding, had previously been rubbed with 1% soya lecithin W250 in ethyl acetate solution and dried. The aluminium dish thus filled is heated in a drying cabinet at 180° C. for 10 min. After cooling to room temperature, the test specimen is demoulded. Test specimens of thickness about 2 mm are obtained.

The following table shows characteristic properties of the products:

| Example | 3 | 4 | 5 | 6 | 7 | 8 |
|---|---|---|---|---|---|---|
| Starting polyisocyanate | A2) | A3) | A4) | A5) | A6) | A7) |
| Appearance | clear | clear | clear | clear | clear | clear |
| Tg [° C.] | 127.7 | 124.9 | 121.4 | 102.5 | 119.0 | 114.2 |
| Shore D hardness | 82 | 79 | 80 | 83 | 82 | 81 |
| Density (20° C.) [g/cm$^3$] | 1.24 | 1.24 | 1.23 | 1.22 | 1.23 | 1.23 |
| Volume shrinkage [%] | 7.3 | 8.9 | 8.1 | 8.2 | 9.8 | 5.8 |

The invention claimed is:

1. A process for producing polyisocyanurate plastics, comprising the following steps:
   a) providing a polyisocyanate composition A) which contains oligomeric polyisocyanates and is low in monomeric diisocyanates, "low in monomeric diisocyanates" meaning that the polyisocyanate composition A) has a content of monomeric diisocyanates of at most 20% by weight;
   b) catalytically trimerizing the polyisocyanate composition A) until at least 95% of free isocyanate groups present in the polyisocyanate composition prior to step b) have reacted.

2. The process according to claim 1, wherein in the oligomeric polyisocyanate a proportion of isocyanurate groups makes up at least 50 mol-% of the sum total of oligomeric polyisocyanates consisting of uretdione, isocyanurate, allophanate, biuret, iminooxadiazinedione and oxadiazinetrione structures.

3. The process according to claim 1, wherein the polyisocyanate composition A) consists to an extent of at least 70% by weight of polyisocyanates having exclusively aliphatically and/or cycloaliphatically bound isocyanate groups.

4. The process according to claim 1, wherein trimerization means cyclotrimerization of at least 50% of the isocyanate groups present in the polyisocyanate composition A) to isocyanurate structural units.

* * * * *